US008683878B2

(12) United States Patent
Secord

(10) Patent No.: US 8,683,878 B2
(45) Date of Patent: Apr. 1, 2014

(54) SAMPLING DEVICE, TRUCK HAVING SAMPLING DEVICE AND METHOD OF SAMPLING DRY BULK

(76) Inventor: Greg Secord, Beaumont (CA)

(*) Notice: Subject to any disclaimer, the term of this patent is extended or adjusted under 35 U.S.C. 154(b) by 357 days.

(21) Appl. No.: 12/335,147

(22) Filed: Dec. 15, 2008

(65) Prior Publication Data

US 2010/0147087 A1    Jun. 17, 2010

(51) Int. Cl.
*G01N 1/20* (2006.01)
(52) U.S. Cl.
USPC ............... 73/863.61; 73/863.41; 73/863.86
(58) Field of Classification Search
USPC ...................................................... 73/863.61
See application file for complete search history.

(56) References Cited

U.S. PATENT DOCUMENTS

| 4,105,420 | A | * | 8/1978 | Moore ............................. 96/416 |
| 4,405,561 | A | * | 9/1983 | Neale et al. .................... 422/145 |
| 4,756,855 | A | * | 7/1988 | Mathis et al. .................. 264/406 |
| 5,580,193 | A |   | 12/1996 | Battle et al. |
| 5,673,737 | A | * | 10/1997 | Behnke et al. ................. 141/372 |
| 6,210,457 | B1 | * | 4/2001 | Siemers ............................ 55/429 |
| 7,121,156 | B2 | * | 10/2006 | Anschutz et al. ........... 73/863.61 |

FOREIGN PATENT DOCUMENTS

JP    06294716 A    * 10/1994

* cited by examiner

*Primary Examiner* — Hezron E Williams
*Assistant Examiner* — Paul West
(74) *Attorney, Agent, or Firm* — O'Shea Getz P.C.

(57) ABSTRACT

A sampling device has a valve body that comprises an inlet for connecting to an unloading pipe of a container containing dry bulk product, the inlet being shaped to receive a flow of dry bulk product from the container. The valve body has a first outlet which, when opened, discharges the dry bulk product that enters the valve body through the inlet. The valve body also has a second outlet which, when opened, discharges a sample of the dry bulk product, the second outlet having a cross-sectional area that is smaller than a cross-sectional area of the first outlet. The sampling device enables a sample of dry bulk product, e.g. cement, slag, fly ash, cement kiln dust, silica fume, silica sand, lime, alumina, flour, or any other similar dry powdery substance to be obtained safely from a transport container or vessel.

15 Claims, 4 Drawing Sheets

SAMPLING DEVICE, TRUCK HAVING SAMPLING DEVICE AND METHOD OF SAMPLING DRY BULK

CROSS-REFERENCE TO RELATED APPLICATIONS

This application claims priority to Canadian Appln. No. 2,646,749 filed on Dec. 12, 2008.

TECHNICAL FIELD

The present technology relates generally to bulk material handling and, in particular, to sampling of dry bulk products such as cement.

BACKGROUND

For many years, truck drivers, plant operation employees, sales representatives and others have been asked to gather a sample of dry bulk or other products from a trailer that is being unloaded. Some facilities have an unloading pipe to which a pipe nipple is welded. The pipe nipple has a valve around which a plastic bag can be wrapped to capture a sample of the dry bulk. While the trailer is being unloaded, the valve is carefully opened to fill the bag with a sample of the dry bulk product. Other facilities have no such pipe nipple, in which case the individual tasked with sampling the dry bulk has to climb on top of the trailer to retrieve a sample. Some operators stand precariously on a pallet lifted up by a forklift (or in the bucket of a front-end loader or of a Bobcat® utility vehicle). The person tasked with retrieving the sample is then raised to a height that enables that person to access the top hatch of the trailer. The raised person must then reach over and open the hatch, and then maintain his balance while retrieving a sample of the dry bulk using a shovel or other tool or implement.

This traditional technique for retrieving a sample of dry bulk from the top hatch of a trailer has led to a number of injuries and safety incidents. Accordingly, a safer way of sampling dry bulk product from a trailer remains highly desirable.

Thus, a main aspect of the present invention is a sampling device having a valve body that includes an inlet for connecting to an unloading pipe of a container containing dry bulk product, the inlet being shaped to receive a flow of dry bulk product from the container. The valve body also includes a first outlet which, when opened, discharges the dry bulk product that enters the valve body through the inlet. The valve body further includes a second outlet which, when opened, discharges a sample of the dry bulk product, the second outlet having a cross-sectional area that is smaller than a cross-sectional area of the first outlet.

Another aspect of the present invention is a truck for transporting dry bulk product. The truck has a container for containing dry bulk product, the container having unloading pipe which can be opened to discharge the dry bulk product from the container, a pneumatic system for pressurizing the container to force the dry bulk product through the unloading pipe, and a sampling device connected to the unloading pipe of the container for sampling dry bulk product from the container. The sampling device includes an inlet for connecting to the unloading pipe of the container, a first outlet which, when opened, discharges the dry bulk product that enters the valve body through the inlet, and a second outlet which, when opened, discharges a sample of the dry bulk product, the second outlet having a cross-sectional area that is smaller than a cross-sectional area of the first outlet.

Yet another aspect of the present invention is a method of sampling dry bulk product. The method entails connecting a sampling device to an unloading pipe of a container containing the dry bulk product, the sampling device having an inlet, a first outlet and a second outlet, wherein a cross-sectional area of the second outlet is smaller than a cross-sectional area of the first outlet, ascertaining that a lid is clamped to a first outlet of the sampling device, and opening a valve to draw off a sample of the dry bulk product through the second outlet of the sampling device.

The details and particulars of these aspects of the invention will now be described below, by way of example, with reference to the attached drawings.

BRIEF DESCRIPTION OF THE DRAWINGS

Further features and advantages of the present technology will become apparent from the following detailed description, taken in combination with the appended drawings, in which.

It will be noted that throughout the appended drawings, like features are identified by like reference numerals.

DETAILED DESCRIPTION

In general, the sampler or sampling device connects to an unloading pipe of a trailer or container to enable dry bulk product to be drawn off as a sample.

Figure 1:
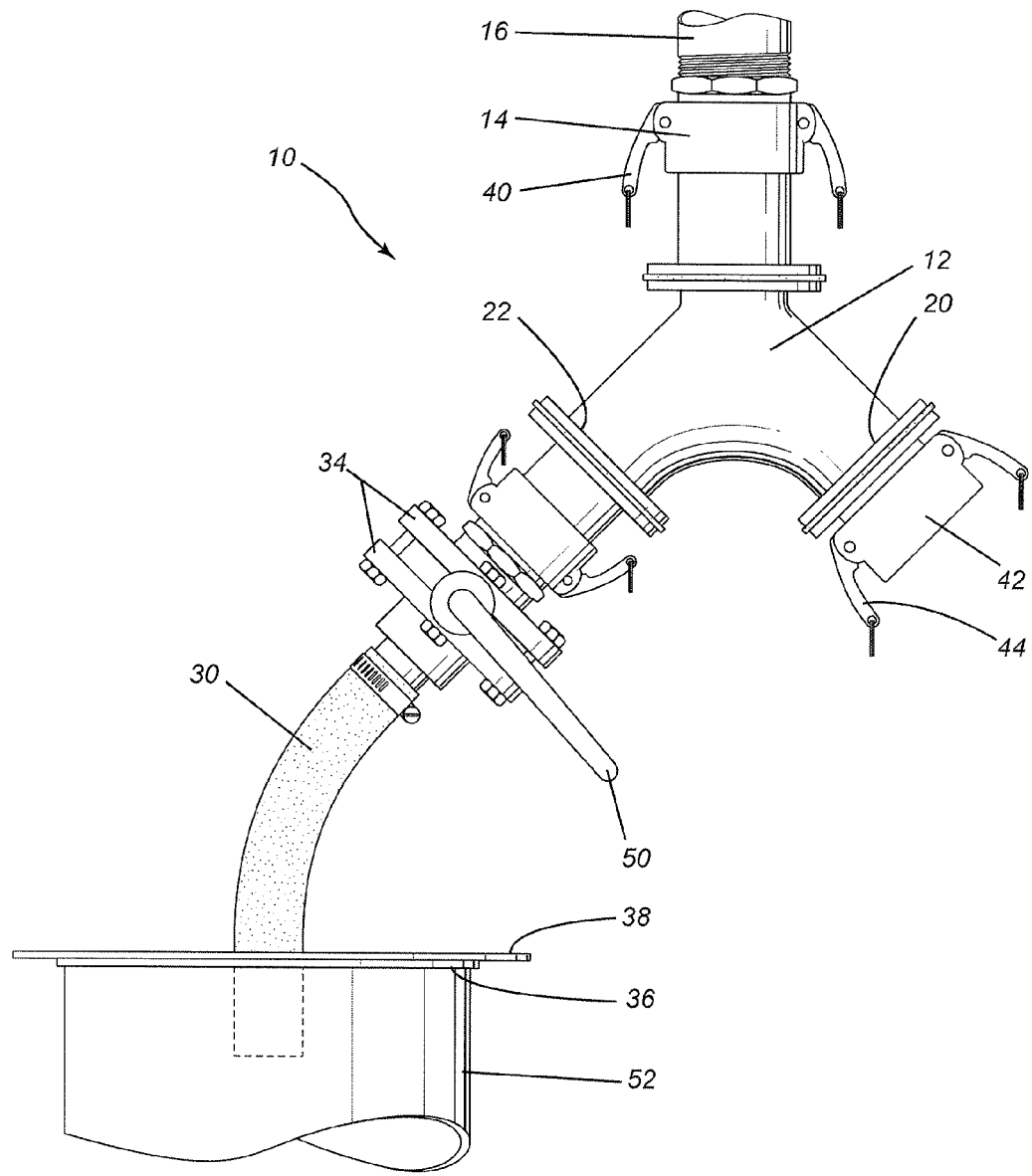
FIG. 1 is a top plan view of a sampling device in accordance with an embodiment of the present invention.
Figure 2:
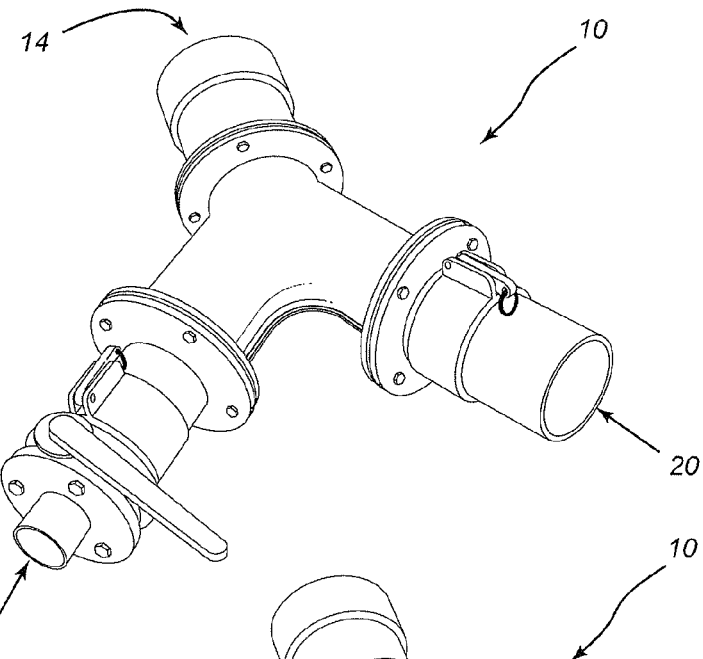
FIG. 2 is an isometric view of the sampling device of FIG. 1.

FIG. 1 is a top plan view of a sampling device, which is designated by reference numeral 10, in accordance with an embodiment of the present invention. FIG. 2 is an isometric view of the sampling device of FIG. 1. With reference to these two figures, the sampling device 10 has a valve body 12 comprising an inlet 14 for connecting to an unloading pipe 16 of a container 18 containing dry bulk product, the inlet 14 being shaped to receive a flow of dry bulk product from the container 18. The valve body 12 has a first outlet 20 which, when opened, discharges the dry bulk product that enters the valve body 12 through the inlet 14. The valve body 12 has a second outlet 22 which, when opened, discharges a sample of the dry bulk product. The second outlet 22 has a cross-sectional area that is smaller than a cross-sectional area of the first outlet 20.

For the purposes of this specification, the expression "dry bulk" or "dry bulk product" is meant to include cement, slag, fly ash, cement kiln dust, silica fume, silica sand, lime, alumina, flour, or any other similar dry powdery substance.

In one embodiment, the sampling device 10 may include a hose 30 (such as for example a braided hose or other flexible tube) having a first end 32 connected to the second outlet 22 by a flanged fitting 34 and having a second end 36 connected to a transparent disc 38 mounted concentrically around the hose via a central hole in the disc.

In one embodiment, the inlet 14 of the sampling device 10 may have a quick-connect clamp 40 for connecting to the unloading pipe 16. The quick-connect clamp may be replaced with any other mechanical fastening means. Although the typical unloading pipe is 4 or 5 inches in diameter, the sampling device can be scaled (made in different sizes) to accommodate any size of unloading pipe. Alternatively, one or more adapters can be provided to fit differently sized pipes.

In one embodiment, the first outlet 20 of the sampling device 10 may have a removable lid 42 and a quick-connect clamp 44 for clamping the outlet to an unloading hose. The quick-connect clamp may be replaced with any other mechanical fastening means.

Figure 3:
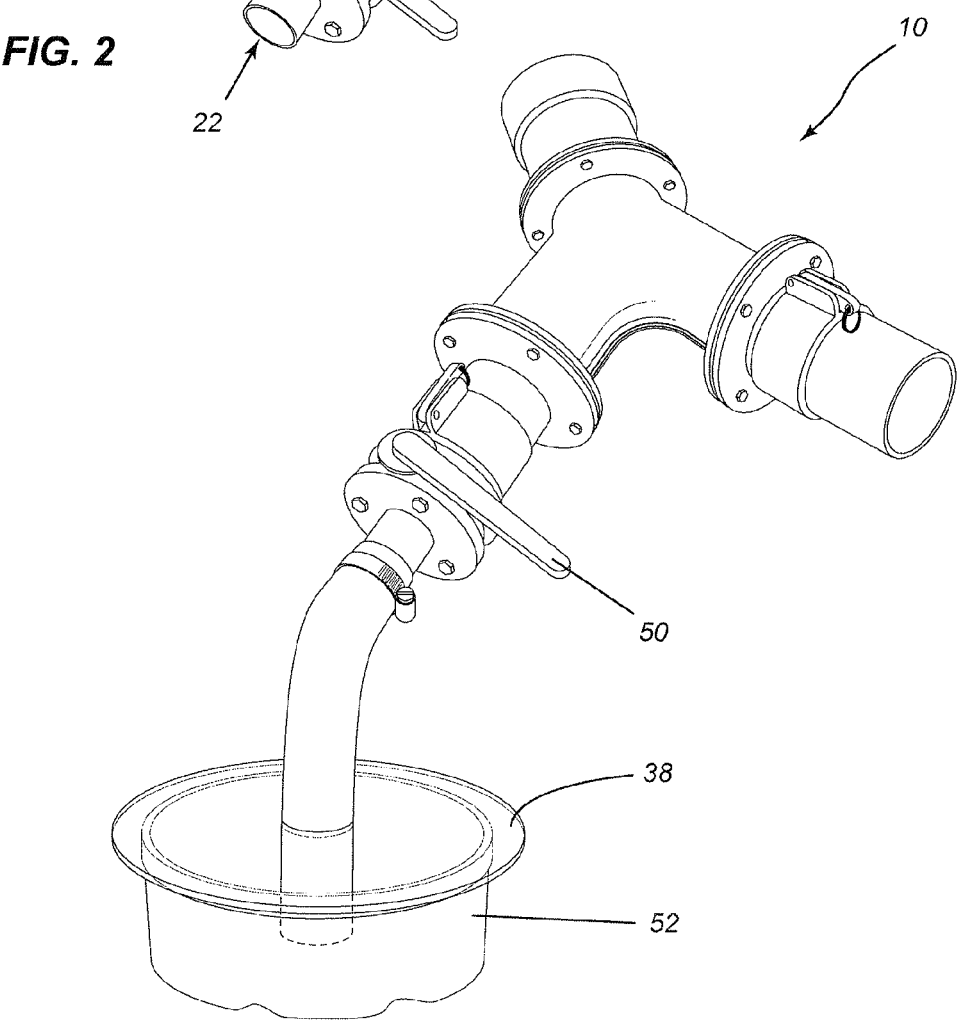
FIG. 3 is an isometric view of the sampling device having a hose for drawing a sample into a barrel or other sample-collecting container.

In one embodiment, the second outlet 22 of the sampling device 10 may have a lever-actuated valve 50 for opening and closing the second outlet 22 to thereby control an outflow of dry bulk product into a sample-collecting container 52. The lever-actuated valve 50 is preferably a butterfly valve. A butterfly valve has been found to work better than other types of valves such as ball valves. The butterfly valve is thus manually actuated to control an amount of dry bulk product drawn off through the second outlet and hose into the bucket, barrel or other sample-collecting container. As depicted in FIG. 1 and FIG. 2, the butterfly valve is mounted between a first flange and a second flange. In other words, the first flange connects to the valve on one side while the second flange is connected to the other side of the valve. The second flange is also attached to the braided hose as shown in FIG. 3. The transparent disc enables the operator to see how much sample has been drawn off. When an appropriate amount has been sampled, the operator shuts off the butterfly valve. Sampling can be done either while the container or trailer is being unloaded or beforehand. For example, for a typical 4 inch pipe, the sampler would have a 1.5 inch butterfly valve, flanges with a 1.5 inch bore and a 1.5 inch braided hose. However, it should be understood that these dimensions can be varied to achieve different flow characteristics.

The sampler (sampling device) can be constructed of cast iron, steel, stainless steel, aluminum, titanium, or one of various alloys, although preferably aluminum or stainless steel would be employed. An aluminum sampler would weigh no more than 26 lbs (approx. 12 kg) and thus is light enough to be carried around and installed by a single operator. The valve body of the sampler can be cast in one or multiple components. Teflon and plastic components can be used for durability and to reduce the overall weight of the device.

Figure 4:
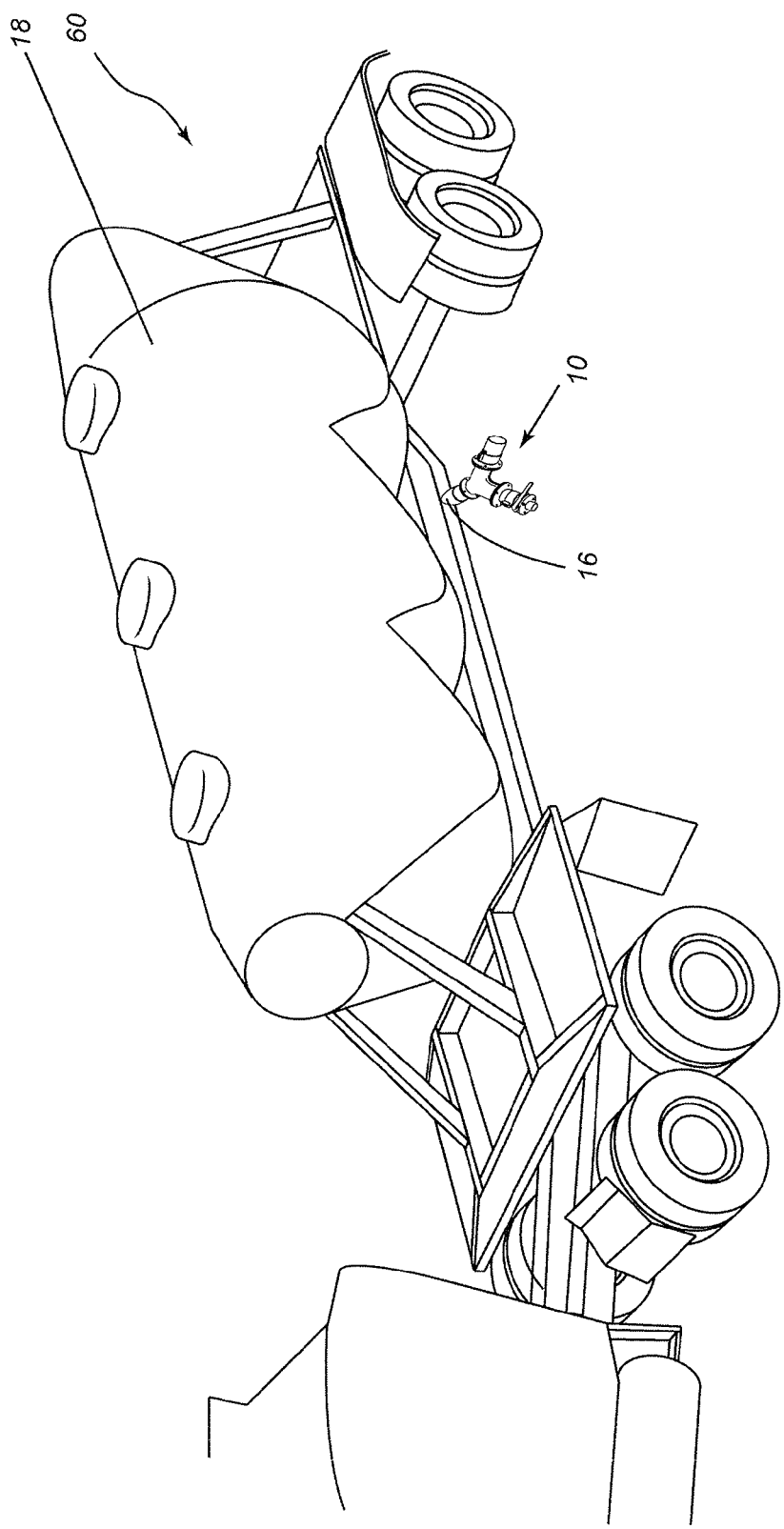
FIG. 4 is an isometric view of a truck having a sampling device mounted to its unloading pipe.

FIG. 4 is an isometric view of a truck 60 having a sampling device 10 mounted to its unloading pipe 16. As depicted in FIG. 4, the truck 60 is e.g. a tractor-trailer or other vehicle designed for transporting dry bulk product. The truck includes a container 18 (or vessel) for containing dry bulk product. The container has an unloading pipe which can be opened to discharge the dry bulk product from the container. A pneumatic system can be provided (not shown in the figures but well known in the art) for pressurizing the container to force the dry bulk product through the unloading pipe. The sampling device 10 described above is then mounted to the unloading pipe for sampling and unloading. As will be appreciated, the truck can come pre-equipped with the sampling device (factor installed) or it can be added as an aftermarket accessory. Alternatively, the sampler can be mounted to a truck only as needed.

Another aspect of this invention is a method of sampling dry bulk product. The method involves using the novel sampler or sampling device. The sampler is connected to an unloading pipe of a container containing the dry bulk product. The user verifies or ascertains that the lid is clamped to the first outlet of the sampling device. This ensures that dry bulk product does not flow out of the device into the unloading hose. The user opens a valve to draw off a sample of the dry bulk product through the second outlet of the sampling device. This can be done by turning the hand lever of the lever-actuated valve to enable dry bulk product to flow out of the valve into a bag, barrel or other sample-collecting container. In one embodiment, the sample is drawn off through a hose, e.g. a braided hose, connected to the second outlet. The braided hose can have a clear plastic circular disc affixed to the distal end of the hose to fit over the barrel or other sample-collecting container (to retain the powdery substance within the barrel or other sample-collecting container (and to prevent the powder from blowing back into the face of the user). Since the disc is transparent, the user can observe the amount of sample accumulating in the barrel or sample-collecting container. The disc can be made of acrylic, polycarbonate or another suitable plastic or polymer.

To displace the dry bulk product through the sampler, the user may pneumatically pressurize the container (vessel) containing the dry bulk product in order to force the dry bulk product through the sampling device. Containers with low-pressure force feed systems (i.e. containers that can be pneumatically pressurized) are well known in the art, and need not be described herein. For example, U.S. Pat. No. 5,580,193 describes a method and system for unloading dry bulk materials from a tank hopper supported on a trailer, the trailer being connected to a tractor. A material conveying conduit receives material from the hopper. A blower supplies pressurized air to the hopper and to the conduit to create a pressure differential between the hopper and the conduit to thereby induce the flow of materials from the hopper to the conduit.

For the purpose of this specification, it should be understood that sampling (or taking a sample) may involve taking of multiple samples (or taking of a single sample in steps).

This sampler can be used to safely draw a sample from a trailer (truck or tractor-trailer), from a rail car, ship, barge, or from any other vehicle that has a container, trailer, hopper or vessel containing dry bulk product and that has an unloading pipe to which the inlet of the novel sampling device can be clamped or otherwise connected. By utilizing this novel sampler to draw off a sample of dry bulk, it is therefore no longer necessary to climb or be hoisted up to access the dry bulk through the top hatch in the container/trailer. Accordingly, usage of this novel sampler is expected to dramatically reduce, or even eliminate, the number of safety incidents that have historically arisen during sampling operations.

Figure 5:
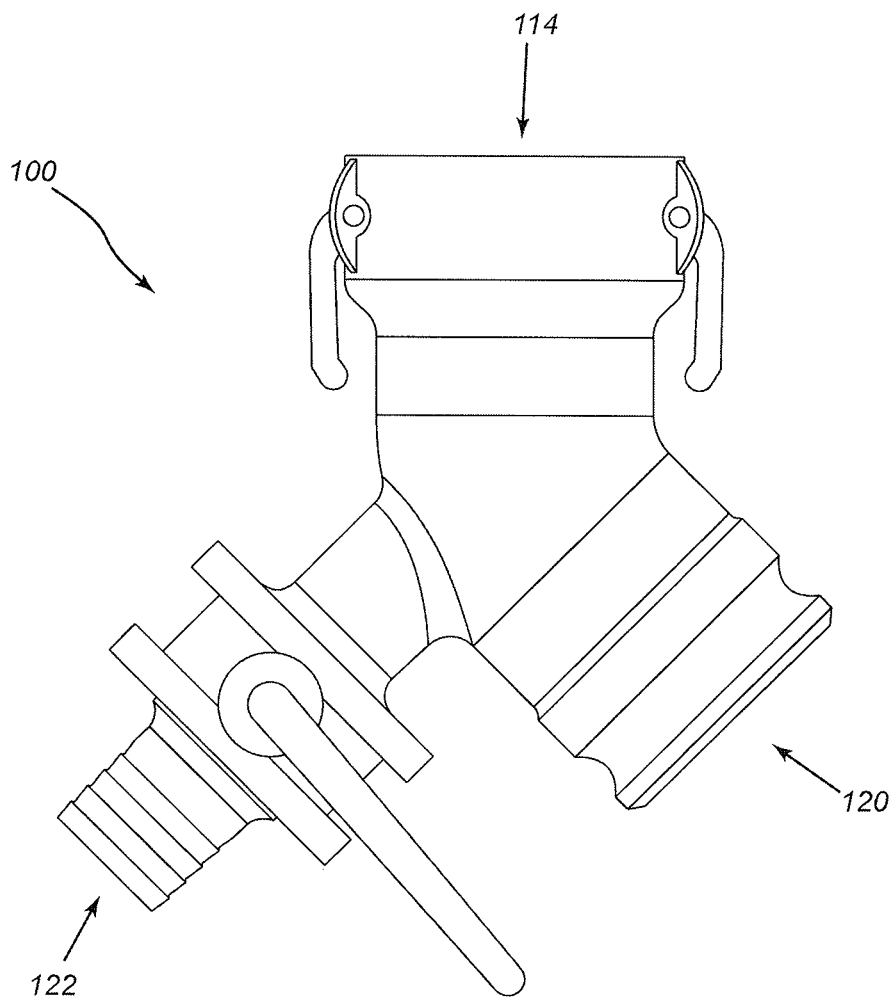
FIG. 5 is a top plan view of another sampling device in accordance with another embodiment of the present invention.

FIG. 5 is a top plan view of another sampling device in accordance with another embodiment of the present invention. This sampling device 100 can be molded of one single piece which eliminates having to bolt together several different pieces. The molded sampling device can be manufactured of aluminum (e.g. AL356) or any other suitable alloy of aluminum). The version of the sampling device 100 shown in FIG. 5 also has an inlet 114, a first outlet 120 and a second outlet 122 having a smaller cross-sectional area. This sampling device 100 functions in the same manner as described above.

This new technology has been described in terms of specific examples, embodiments, implementations and configurations which are intended to be exemplary only. Persons of ordinary skill in the art will appreciate that obvious variations, modifications and refinements can be made without departing from the scope of the present invention. The scope of the exclusive right sought by the Applicant is therefore intended to be limited solely by the appended claims.

What is claimed is:

1. A sampling device having a valve body comprising:
an inlet for connecting to an unloading pipe of a container containing dry bulk product, the inlet being shaped to receive a flow of dry bulk product from the container;
a first outlet having a removable lid which, when opened, discharges the dry bulk product that enters the valve body through the inlet while the inlet remains open;
a second outlet having a valve which, when opened, discharges a sample of the dry bulk product while the inlet remains open, the second outlet having a cross-sectional area that is smaller than a cross-sectional area of the first outlet, wherein the first and second outlets are each angled with respect to the inlet, the valve being the only valve in the sampling device; and
a flexible hose having a first end connected to the second outlet by a flanged fitting and having a second end connected to a transparent disc mounted concentrically around the hose via a central hole in the transparent disc, wherein the disc is entirely flat and planar.

2. The sampling device as claimed in claim 1 wherein the inlet comprises a quick-connect clamp for connecting to the unloading pipe.

3. The sampling device as claimed in claim 1 wherein the first outlet comprises a quick-connect clamp for clamping the first outlet to an unloading hose.

4. The sampling device as claimed in claim 3 wherein the second outlet comprises a lever-actuated valve for opening and closing the second outlet to thereby control an outflow of dry bulk product into a sample-collecting container.

5. The sampling device as claimed in claim 1 wherein the valve is a butterfly valve.

6. The sampling device as claimed in claim 1 wherein the second outlet comprises a first flange for connecting to a lever-actuated valve that is also connected to a second flange attached to a hose, the lever-actuated valve being manually actuated to control an amount of dry bulk product drawn off through the hose.

7. A truck for transporting dry bulk product, the truck comprising:
a container for containing dry bulk product, the container having unloading pipe which can be opened to discharge the dry bulk product from the container;
a pneumatic system for pressurizing the container to force the dry bulk product through the unloading pipe; and
a sampling device connected to the unloading pipe of the container for sampling dry bulk product from the container, the sampling device comprising:
an inlet for connecting to the unloading pipe of the container;
a first outlet having a removable lid which, when opened, discharges the dry bulk product that enters a valve body through the inlet while the inlet remains open;
a second outlet having a valve which, when opened, discharges a sample of the dry bulk product while the inlet remains open, the second outlet having a cross-sectional area that is smaller than a cross-sectional area of the first outlet, wherein the first and second outlets are each angled with respect to the inlet, the valve being the only valve in the sampling device; and
a flexible hose having a first end connected to the second outlet by a flanged fitting and having a second end connected to a transparent disc mounted concentrically around the hose via a central hole in the transparent disc, wherein the disc is entirely flat and planar.

8. The truck as claimed in claim 7 wherein the second outlet comprises a first flange for connecting to a lever-actuated valve that is also connected to a second flange attached to a hose, the lever-actuated valve being manually actuated to control an amount of dry bulk product drawn off through the hose.

9. The truck as claimed in claim 7 wherein the inlet comprises a quick-connect clamp for connecting to the unloading pipe.

10. The truck as claimed in claim 7 wherein the first outlet comprises a quick-connect clamp for clamping the first outlet to an unloading hose.

11. The truck as claimed in claim 7 wherein the valve is a butterfly valve.

12. A method of sampling dry bulk product, the method comprising:
connecting an inlet of a sampling device to an unloading pipe of a container containing the dry bulk product, the sampling device having an inlet, a first outlet having a removable lid and a second outlet having a valve, wherein a cross-sectional area of the second outlet is smaller than a cross-sectional area of the first outlet and wherein the first and second outlets are each angled with respect to the inlet, the valve being the only valve in the sampling device; and
opening the valve on the second outlet to draw off a sample of the dry bulk product through the second outlet of the sampling device while the inlet remains open, wherein the sample flows through a flexible hose connected to the second outlet, the hose extending through a central hole in a transparent disc mounted concentrically around the hose, wherein the disc is entirely flat and planar.

13. The method as claimed in claim 12 comprising blocking the first outlet with the removable lid wherein the sample is drawn off through the hose connected to the second outlet while the dry bulk product is blocked from concurrently flowing through the first outlet.

14. The method as claimed in claim 12 further comprising pneumatically pressurizing the container containing the dry bulk product in order to force the dry bulk product flowing from the inlet through the sampling device.

15. The method as claimed in claim 12 comprising concurrently discharging the dry bulk product through the first outlet.

* * * * *